United States Patent [19]
Groth

[11] Patent Number: 5,480,303
[45] Date of Patent: Jan. 2, 1996

[54] GINGIVAL RETRACTION CORD TOOL

[75] Inventor: Eric Groth, Camarillo, Calif.

[73] Assignee: Belport Company, Inc., Camarillo, Calif.

[21] Appl. No.: 290,616

[22] Filed: Aug. 15, 1994

[51] Int. Cl.$^6$ ..................................................... A61C 5/14
[52] U.S. Cl. ........................................... 433/136; 433/141
[58] Field of Search .................................... 433/136, 138, 433/139, 141, 3; 606/113, 139, 144, 148; 140/118, 119, 120

[56] References Cited

U.S. PATENT DOCUMENTS

| 2,943,650 | 7/1960 | Rubin | 140/119 |
| 3,759,302 | 9/1973 | Attenborough | 140/119 |
| 4,247,285 | 1/1981 | Roig-Greene | 433/141 |

FOREIGN PATENT DOCUMENTS

| 2481595 | 11/1981 | France | 433/3 |

Primary Examiner—Cary E. O'Connor
Attorney, Agent, or Firm—Jack C. Munro

[57] ABSTRACT

A gingival retraction cord tool comprising a handle which has a front end formed into an elongated barrel and a rear end formed into an enlarged body. The enlarged body includes an outer end which is movable relative to the elongated barrel. Extending through the elongated barrel and the enlarged body is a through hole and located within that through hole is a length of gingival retraction cord. From the front end of the elongated barrel the retraction cord is formed into a closed loop. Movement of the outer end is between a locked position and an unlocked position. When in the locked position the cord is not movable relative to the elongated barrel and when in the unlocked position the cord is movable relative to the elongated barrel. The loop is to be placed around a tooth with the cord to be moved relative to the handle to decrease the size of the loop and snugly locate the cord about the tooth. The loop is then further decreased in size by twisting of the handle to tightly locate the loop on the tooth. The cord is then physically packed between the gum and the tooth.

4 Claims, 1 Drawing Sheet

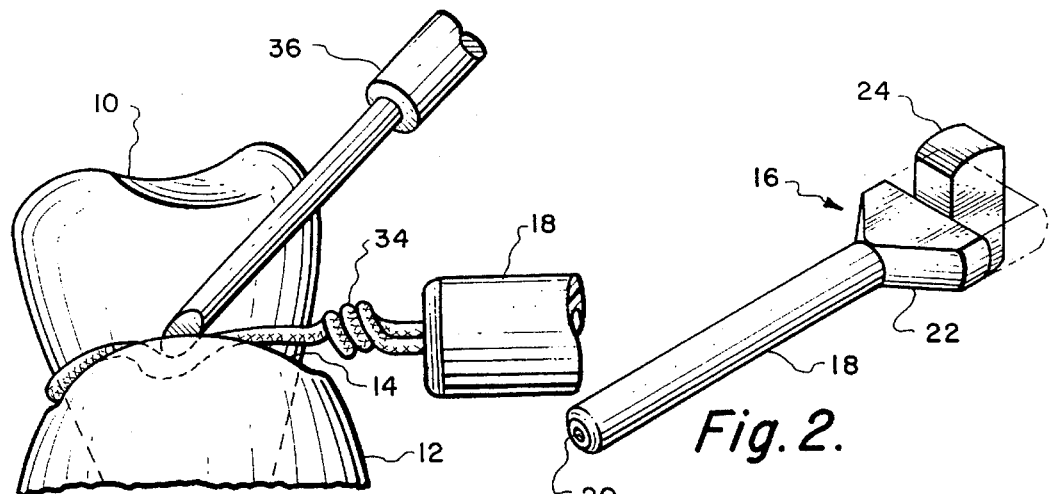
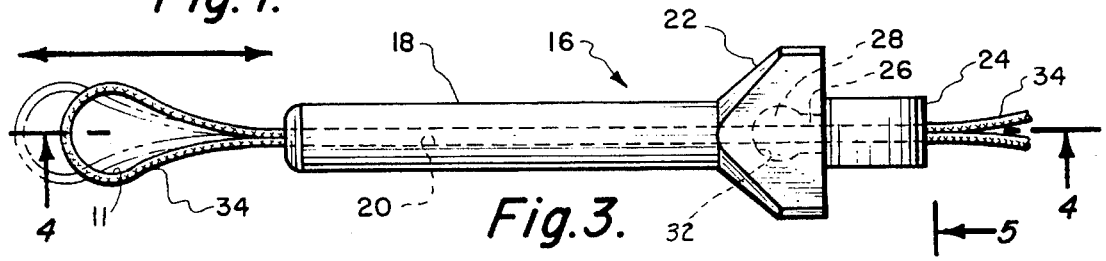
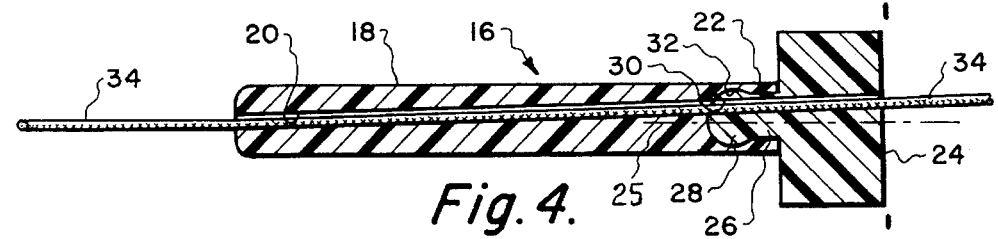
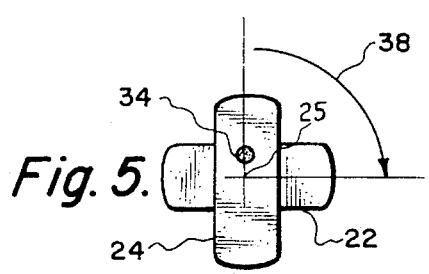
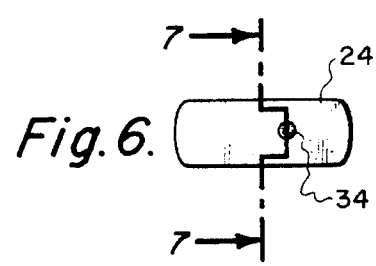
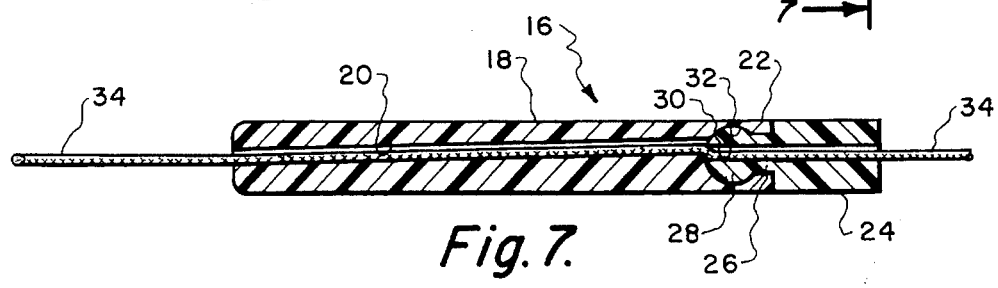

5,480,303

GINGIVAL RETRACTION CORD TOOL

BACKGROUND OF THE INVENTION

1. Field of the Invention

The field of this invention relates to tools and more particularly to a tool for applying gingival retraction cord by a dentist in conjunction with human teeth and gums.

2. Description of the Prior Art

Gingival retraction cord has long been in use by dentists. The gingival retraction cord is used by being wrapped around the tooth and then packed into the sulcus by the dentist or dental technician (user). The cord can be unimpregnated and have the purpose of just locating the gums spaced from the tooth permitting the user access to the tooth located beneath the gum line. The cord can also be impregnated with an astringent, antiseptic, antibiotic, hemostyptic or other type of solution for the purpose of supplying an ingredient to the sulcus. Gingival retraction cord is commonly used by dentists to retract the gum from the tooth so as to facilitate preparation of a tooth for an impression to create a prosthetic.

A typical procedure for supplying gingival retraction cord to the user is by a container that contains a given quantity of cord. The user opens the container, pulls out a given length of cord and sever the cord with a knife or scissors. The user then takes the cord and carefully wraps it around the tooth and while holding the ends of the cord with one hand, takes a tool and packs the retraction cord into the sulcus. One problem with this procedure is that it is time consuming. Also, a substantial length of retraction cord is utilized which is greater what is actually needed, therefore creating waste. There is a need to design a tool which facilitates the application of the retraction cord and its insertion within the sulcus.

Previous to this invention there was applicator that was designed by the present inventor upon which a U.S. patent application Ser. No. 08/157,410 was filed. This application was entitled Gingival Retraction Cord Applicator and it was filed on Nov. 26, 1993. This applicator comprises an elongated handle from which protrudes at one end a loop of cord. The loop is to be placed around the tooth and then the handle twisted until the cord becomes snug about the tooth and then the cord is packed into the sulcus. The primary disadvantage of this applicator is that there is no way to adjust the size dimension of the loop. Therefore, if the loop was placed around a small tooth, it would be necessary for the dentist or dental technician to twist the handle a substantial number of times in order for the cord to finally become snug about the tooth. This time consuming procedure of twisting a substantial number of times has been eliminated by the present invention in that the cord is capable of being initially adjusted substantially in a snug manner about the tooth prior to initiating of the twisting action. Therefore, only one or two twists are required to make the cord snug about the tooth.

SUMMARY OF THE INVENTION

The tool of the present invention utilizes a handle composed of an elongated barrel and an enlarged body with the enlarged body located at the rear of the handle. The enlarged body includes an outer end which is pivotally mounted to the remaining portion of the enlarged body. Extending entirely through the enlarged body (including the outer end) and the elongated barrel is a through hole. Two ends of a cord is conducted through the through hole forming a loop protruding exteriorly of the front end of the elongated barrel. The outer end can be moved between a locked position and an unlocked position. When in the unlocked position, the cord can be manually moved within the through hole. When in the locked position, the cord is not able to be moved within the through hole.

The primary objective of the present invention is to incorporate an adjustable loop of gingival retraction cord in conjunction with a tool with this tool being easily usable to wrap the cord around a tooth facilitating the placement of the gingival retraction cord within the sulcus.

Another objective of the present invention is to construct a tool which is sufficiently inexpensive to permit single usage by the user and then disposed of thereby minimizing the possibility of cross contamination between patients.

Another objective of the present invention is to construct a tool which can be easily and quickly operated not requiring any special skill.

BRIEF DESCRIPTION OF THE DRAWING

FIG. 1 is a view depicting usage of the tool of the present invention in conjunction with a tooth showing packing of the gingival retraction cord within the sulcus;

FIG. 2 is an isometric view of the tool of the present invention where the outer end of the enlarged body is positioned in the unlocked position;

FIG. 3 is a top plan view of the tool of the present invention in the position shown in FIG. 2;

FIG. 4 is a longitudinal cross sectional view of the tool of the present invention taken along line 4—4 of FIG. 3;

FIG. 5 is a rear view of the tool of the present invention taken along line 5—5 of FIG. 4;

FIG. 6 is a rear view similar to FIG. 5 but showing the outer end in the locked position; and FIG. 7 is a cross-sectional view similar to FIG. 4 but where the outer end is in the locked position.

DETAILED DESCRIPTION OF THE SHOWN EMBODIMENT

Referring particularly to the drawing, there is shown a tooth 10 being mounted within a gum 12, with it being understood that normally there would be a plurality of teeth 10 within the mouth of the human. The tooth 10 protrudes above the gum line 14 of the gum 12. Between the gum line 14 and the tooth 10 there is located the sulcus, with this portion of the gum 12 being expandable to move away from the tooth 10.

The tool 16 of this invention comprises a cylindrically shaped elongated barrel 18 which will normally constructed of a plastic material with generally Delrin® being preferred. The elongated barrel 18 has a front end within which is located one end of a through hole 20. Integrally connected to the rear end of the elongated barrel 18 is an enlarged body 22. A portion of the enlarged body 22 is integrally connected to the elongated barrel 18.

Formed interiorly of the enlarged body 22 that is integrally connected to the elongated barrel 18 is a socket 32. The through hole 20 connects with the socket 32. However, this connection of the through hole 20 with the socket 23 is shown to be "off center" that is spaced from the longitudinal center axis 25 of the elongated barrel 18.

Pivotally mounted within the socket 32 is a ball 28. The ball 28 also includes a hole 30 which forms part of the through hole 20. The ball 28 closely conforms to the socket 32 but is readily capable of pivotal movement within the socket 32. Connecting with the ball 28 is a necked down section 26 which integrally connects to an outer end 24. The hole 30 extends through the outer end 24. The exterior configuration of the outer end 24 is basically similar to that of the enlarged end 22 that is integrally connected to the elongated barrel 18. Therefore, the outer end 24 can be pivoted to a position which aligns with the fixed portion of the enlarged end 22 and in essence form a single part. This position is shown in FIGS. 6 and 7 of the drawings and this is referred to as the locked position. However, the outer end 24 can then be moved counterclockwise, when observing FIG. 5, and this position is shown in FIGS. 2, 3 and 4 of the drawing. This is to be referred to as the unlocked position. When observing FIG. 5, if the outer end 24 is moved clockwise, as represented by arrow 38, to the position shown in FIG. 6, the outer end 24 will then be in the locked position. If the outer end 24 is moved an additional ninety degrees or even an additional one hundred and eighty degrees, the outer end 24 will still remain in the locked position. Only when the outer end 24 occupies the position shown in FIGS. 4 and 5 will the outer end 24 be in the unlocked position.

The ends of the cord 34 are located in juxtaposition and conducted through the through hole 20. With the ends of the cord 34 in juxtaposition and located within the through hole 20 there is formed a loop 11. It is that loop 11 that is located about the tooth 10.

The user will initially acquire the tool 16 with the cord 34 being locked with the outer end in the position shown in FIG. 7. When in this locked position, the portion of the through hole 30 is misaligned from the through hole 20 located within the elongated barrel 18. This misalignment creates a binding action in the area of the socket 32. It is this binding action that locks or fixes the position of the cord 34.

Normally the tool 16 will be shipped to the user in a sterile or clean package. The tool 16 will be removed from the package by the user and the loop 11 placed around the tooth 10. The user will then hold with one hand the elongated barrel 18 and with the opposite hand pivot the outer end 24 ninety degrees. The user will then grasp the rear end of the cord 34 that extends exteriorly of the outer end 24 pulling the loop 11 tight about the tooth 10. At this particular time the user will then twist the outer end 24 ninety degrees which will then cause the binding action to again occur and lock the position of the cord 34. The user then turns the tool 16 forming a twist within the cord 34 as is clearly shown in FIG. 1 and snugly locates the portion of the cord 34 about the tooth 10 at the gum line 14. The user then takes a separate implement 36 to pack the cord 34 within the sulcus as is depicted within FIG. 1.

When the cord 34 is completely packed within the sulcus, the user can then merely release the handle which is composed of the elongated barrel 18 and the enlarged body 22 with the tool 16 assuming a hanging position. Normally this hanging position will occur for a certain period of time such as five minutes to one half hour which is sufficient time to permit any impregnated solution within the cord 34 to perform its desired function in the area of the sulcus. When it is desired to remove the cord 34, easy removal is accomplished by merely grasping of the handle of the tool 16 and disengaging of the cord 34 from the tooth 10. If the user desires, the cord 34 can be severed in the area of the twisted section of the cord with the tool 16 then being discarded. When it is desired to remove the cord 34 from the sulcus, the dentist or dental technician will take a pair of tweezers and clamp onto a section of the cord 34 and disengage such from the tooth 10.

What is claimed is:

1. A gingival retraction cord tool comprising:

a handle having a front end and a rear end, said handle including an elongated barrel located at said front end and an enlarged body located at said rear end, said enlarged body being fixed to said elongated barrel, said elongated barrel having a longitudinal center axis, a through hole formed through said elongated barrel and said enlarged body, said through hole at said enlarged body being spaced from said longitudinal center axis;

said enlarged body having an outer end, said outer end being connected by connection means to said enlarged body, said outer end being movable by said connection means relative to said enlarged body, movement of said outer end is between a locked position and an unlocked position; and a cord conducted through said through hole, said cord protruding exteriorly of said through hole both from said front end and said rear end, said cord that protrudes from said front end comprising a loop, with said outer end in said locked position said cord being fixed to said elongated barrel, with said outer end in said unlocked position said cord being slidingly movable within said through hole, whereby said-loop is to be placed around a tooth with said cord located against the gum supporting the tooth and then said cord is tightened on the tooth by turning of said handle which twists said cord decreasing the size of said loop with said cord being then packed between the gum and the tooth.

2. The gingival retraction cord tool as defined in claim 1 wherein:

said locked position misaligns the portion of said through hole in said outer end from the portion of said through hole in said elongated barrel.

3. The gingival retraction cord tool as defined in claim 2 wherein:

said outer end being pivotally mounted on said enlarged body.

4. The gingival retraction cord tool as defined in claim 3 wherein:

said connection means comprising a ball and socket.

* * * * *